United States Patent
Brunner et al.

(10) Patent No.: US 7,416,706 B2
(45) Date of Patent: Aug. 26, 2008

(54) LEVEL SENSOR APPARATUS FOR DETECTING CONTACT OF A PIPETTING NEEDLE WITH A LIQUID IN A VESSEL

(75) Inventors: Markus Brunner, Breitenbach (CH); Jürg Dual, Zumikon (CH); Olivier Elsenhans, Sins (CH); Frank May, Zürich (CH); Vuk Siljegovic, Mettmenstetten (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 589 days.

(21) Appl. No.: 11/128,542

(22) Filed: May 13, 2005

(65) Prior Publication Data

US 2006/0093525 A1    May 4, 2006

(30) Foreign Application Priority Data

May 14, 2004  (EP)  .................. 04076435

(51) Int. Cl.
*G05D 9/12* (2006.01)
*B01L 3/02* (2006.01)

(52) U.S. Cl. ............... 422/106; 422/100; 422/105; 422/107; 422/108; 73/863.32; 73/864; 73/864.01; 73/864.02; 73/864.24; 73/427; 222/198; 222/230

(58) Field of Classification Search ............ 422/100, 422/105–108; 73/863.32, 864, 864.01, 864.02, 73/864.24, 427; 222/198, 230, 200, 243
See application file for complete search history.

(56) References Cited

U.S. PATENT DOCUMENTS

| 4,790,183 | A | | 12/1988 | Pfost et al. ................. 73/290 |
| 4,974,458 | A | * | 12/1990 | Koike ..................... 73/864.25 |
| 5,005,434 | A | * | 4/1991 | Watanabe et al. ......... 73/864.21 |
| 5,582,798 | A | * | 12/1996 | Meltzer .................... 422/100 |
| 5,750,881 | A | * | 5/1998 | Dorenkott et al. ............ 73/37 |

(Continued)

FOREIGN PATENT DOCUMENTS

DE   43 16 148 A1   11/1994

OTHER PUBLICATIONS

European Search Report for EP 04 07 6435.9 dated Mar. 12, 2004.

(Continued)

*Primary Examiner*—Brian R. Gordon
(74) *Attorney, Agent, or Firm*—McDonnell Boehnen Hulbert & Berghoff LLP

(57) ABSTRACT

A level sensor apparatus is disclosed for detecting contact of a pipetting needle with a liquid contained in a vessel. The apparatus includes a sensor head made up of a pipetting needle, a needle holder, and an electromechanical transducer. The sensor head also has an associated mechanical resonance frequency. An electrical signal generator is used to generate a driving signal which when applied to the electromechanical transducer causes vibration of the pipetting needle at the resonance frequency. A measurement device is used to measure a parameter of a vibration signal indicative of the mechanical vibration of the pipetting needle when it is driven by the driving signal. An electronic circuit and associated computer software is provided to evaluate variation of the vibration signal with time and thus detect contact of the pipetting needle with a liquid contained in the vessel.

22 Claims, 13 Drawing Sheets

U.S. PATENT DOCUMENTS

| | | | |
|---|---|---|---|
| 5,919,706 A * | 7/1999 | Tajima | 436/54 |
| 6,232,129 B1 * | 5/2001 | Wiktor | 436/180 |
| 6,874,699 B2 * | 4/2005 | Larson et al. | 239/102.1 |
| 7,097,810 B2 * | 8/2006 | Chang et al. | 422/100 |
| 7,125,727 B2 * | 10/2006 | Massaro | 436/180 |
| 7,258,480 B2 * | 8/2007 | Dunfee et al. | 366/197 |
| 7,303,728 B2 * | 12/2007 | Boillat et al. | 422/100 |
| 2002/0150511 A1 * | 10/2002 | Wiktor | 422/100 |
| 2002/0189324 A1 | 12/2002 | Lipscomb et al. | 73/37 |
| 2005/0095723 A1 * | 5/2005 | DiTrolio et al. | 436/180 |

OTHER PUBLICATIONS

Dual, Jürg, "Micro- and Nanomechanics," IMES, Seite 1 von 24, http://www.zfm.ethz.ch/e/res/mic/ printed Jul. 27, 2004.

Dual, Jürg, "Mirco- and Nanomechanics," IMES, Seite 1 von 24, http://www.zfm.ethz.ch/e/res/mic/ printed Jul. 27, 2004, published Sep. 16, 2002.

* cited by examiner

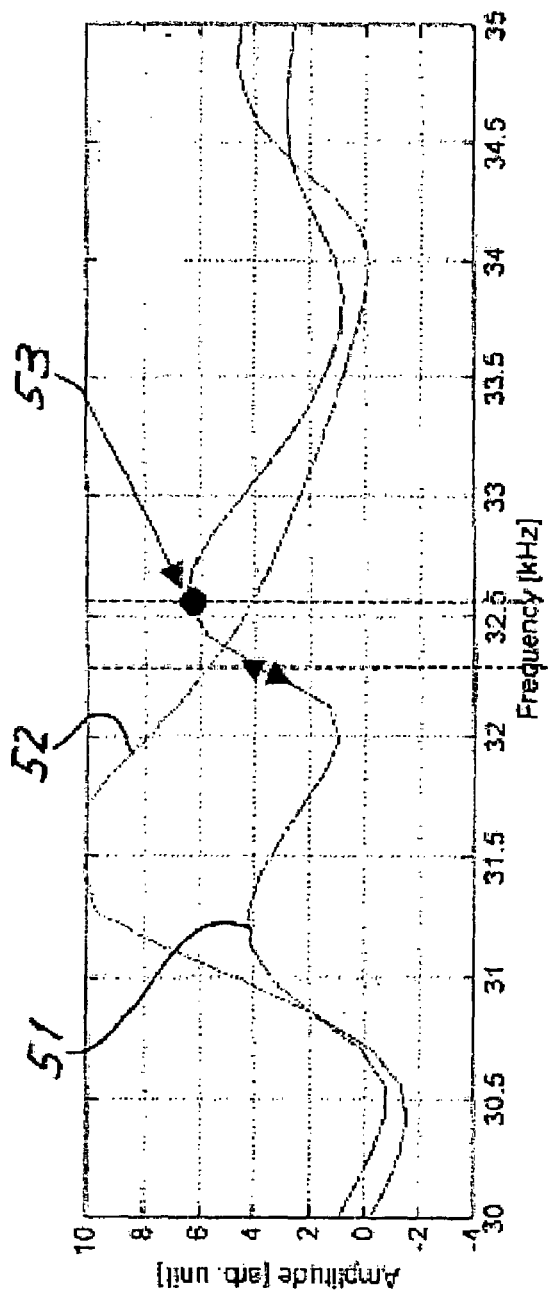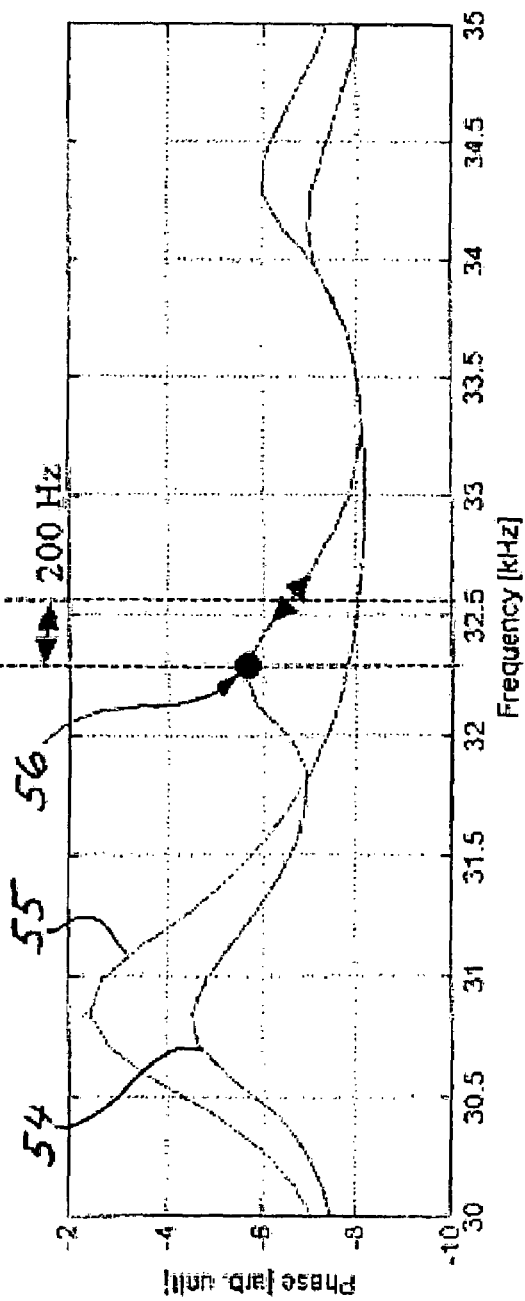
Fig. 10
Fig. 11

LEVEL SENSOR APPARATUS FOR DETECTING CONTACT OF A PIPETTING NEEDLE WITH A LIQUID IN A VESSEL

APPLICATION PRIORITY INFORMATION

This application claims the benefit of European Patent Application Number EP 04076435.9 filed on May 14, 2004.

FIELD OF THE INVENTION

The invention concerns a level sensor apparatus for detecting contact of a pipetting needle with a liquid contained in a vessel.

The invention further concerns a pipetting apparatus for pipetting liquid volumes into and from a liquid contained in a vessel by means of a pipetting needle, and the latter apparatus comprises a level sensor apparatus of the above mentioned kind.

BACKGROUND

Liquid level detection plays an important role for automated chemical analyzers and provides better control of the pipetting process. For performing pipetting operations, a pipetting needle contacts liquid contained in a vessel either for aspirating a sample thereof or for delivering a volume of another liquid to the liquid in the vessel. In order to reduce carry over and to achieve the desired accuracy of a pipetting system it is necessary to minimize contact of the pipetting needle with a vessel's content. Liquid level detection plays an important role for this purpose.

Most liquid level detection methods are reliable under many circumstances but fail when operation of the pipetting systems includes piercing of a vessel's closure with the pipetting needle or when the pipetting needle encounters foam before it reaches the surface of a liquid contained in a vessel.

In the case of liquid containers closed with a cover, such as those used for storage of reagents, the level sensor of the pipetting system should be able to detect a liquid surface that lies under a cover or closure (membrane, foil) of the container. A capacitive level sensor, widely used in chemical analyzers, does not work properly in that case and erroneously indicates detection of a liquid surface when it meets a wet cover. Capacitive liquid detectors also often erroneously detect foam lying on a liquid surface as if it were a liquid surface.

SUMMARY

A first aspect of the invention provides a level sensor apparatus which is able to reliably detect contact between a pipetting needle with a liquid contained in a vessel, even if the pipetting needle has to pierce a cover of the vessel in order to reach the liquid surface and/or even if the pipetting needle has to pass through foam in order to reach the liquid surface.

The first aspect may be embodied by a sensor apparatus that has a sensor head with a known mechanical resonance frequency. The sensor head comprises a pipetting needle attached to a needle holder and mechanically connected to an electromechanical transducer. An electrical signal generator is configured to provide a driving signal to the electromechanical transducer. Similarly, a measurement device is configured to measure a parameter of an electrical signal provided by the electromechanical transducer. The electrical signal provided by the electromechanical transducer is useful because it is indicative of a vibration of the pipetting needle when the vibration is driven by the driving signal. The embodiment further includes an electronic circuit for evaluating variation over time of said parameter of the electrical signal provided by the electromechanical transducer. The variation may be useful for detecting contact of the pipetting needle with a liquid contained in the vessel. The electronics may also be used to provide a resulting signal indicative of the results of the evaluation.

A second aspect of the invention further provides a level sensor apparatus which makes it possible to verify whether a pipetting needle is present or absent in a pipetting apparatus, whether such a pipetting needle has a deformation and/or whether there is an undesirable contact of the pipetting needle with a body.

A third aspect provides a pipetting apparatus for pipetting liquid volumes into and/or from a liquid contained in a vessel by means of a pipetting needle. The apparatus may include an apparatus for sensing a liquid surface in the vessel.

BRIEF DESCRIPTION OF THE DRAWINGS

The subject invention will now be described in terms of several embodiments with reference to the accompanying drawings. These embodiments are set forth to aid the understanding of the invention, but are not to be construed as limiting.

FIG. 10 is a graph showing an example of vibration signal amplitude as a function of vibration frequency.

FIG. 11 is a graph showing an example of vibration signal phase as a function of vibration frequency.

DETAILED DESCRIPTION OF THE DRAWINGS

Figure 1:
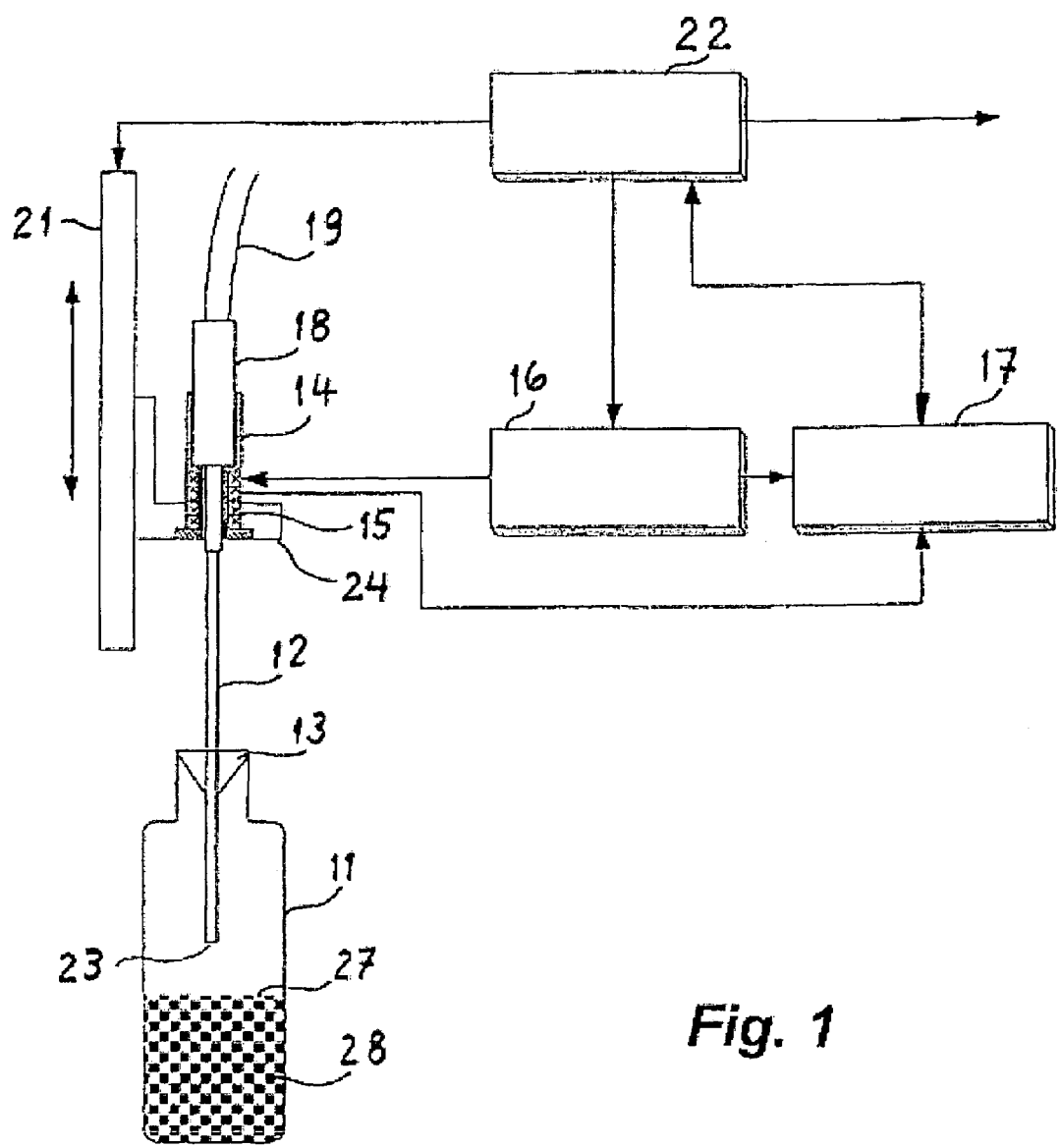
FIG. 1 is a block diagram showing a pipetting apparatus according to an embodiment of the invention.

A level sensor apparatus according to a first aspect of the invention is described hereinafter as a part of a pipetting apparatus. Such a level sensor apparatus is however suitable for uses other than the one described below as example.

A pipetting apparatus according to a second aspect of the invention is described hereinafter with reference to FIGS. 1 to 13. This pipetting apparatus is suitable for dispensing a liquid volume into a vessel 11 by means of a pipetting needle 12 which is suitable for piercing a cover or closure 13 of the vessel. The pipetting apparatus shown by FIG. 1 comprises a level sensor apparatus for detecting contact of pipetting needle 12 with the surface 27 of a liquid 28 contained in vessel 11.

As shown by FIG. 1 a pipetting apparatus according to a second aspect of the invention comprises
 a sensor head including a pipetting needle 12, a needle holder 14 and an electromechanical transducer 15,
 a generator 16 for generating an electrical driving signal which is applied to electromechanical transducer 15 for causing a vibration of pipetting needle 12 at a predetermined frequency,
 an electronic circuit 17 for level detection by processing an output signal of electromechanical transducer 15—the signal being representative of vibration of pipetting needle 12,
 a connecting piece 18, which connects the needle 12 with a conduit 19, which connects the needle 11 with a source of overpressure or under pressure,
 a transport system 21 for transporting needle holder 14, and
 a control unit 22 for controlling the operation of the entire system.

The pipetting needle 12 is preferably made of steel and a large elongated part of its length has a constant cross-section. This elongated part of needle 12 may extend over more than one half of the total length of needle 12. In a preferred embodiment the portion of needle 12 that ends in a delivery tip 23 has a narrower cross-section than the above mentioned elongated part of needle 12. The end of pipetting needle 12 which is opposite to its delivery tip is attached (e.g. bolted) on needle holder 14. Needle holder 14 and pipetting needle 12 are thus interconnected.

The structure of the above mentioned sensor head is configured and dimensioned for substantially maximizing the amplitude of vibrations at the delivery tip 23 (free tip) at a resonance frequency of the sensor head. The resonance frequency may be substantially determined by the dimensions and mechanical properties of needle 12. The transducer 15 is directly coupled to the needle 12 in order to improve the quality factor of the resonance.

In a preferred embodiment pipetting needle 12 is so mounted that it is exchangeable without having to remove electromechanical transducer 15. Electromechanical transducer 15 may, for instance, be a piezoelectric transducer mechanically connected to the pipetting needle 12. This piezoelectric transducer comprises one or more piezoelectric elements. The piezoelectric transducer 15 is clamped or glued (or otherwise attached) to pipetting needle 12 as a way to achieve a proper mechanical contact for the generation of length mode or bending mode vibration of pipetting needle 12 and for accurate measurement of these vibrations.

In a preferred embodiment the piezoelectric transducer 15 and its mechanical coupling to the pipetting needle 12 are adapted for causing a length mode vibration of pipetting needle 12. For this purpose the piezoelectric transducer 15 is preferably a piezoelectric tubus or a stack of piezoelectric rings which is polarized in an axial direction, so that the vibration is performed mainly in a length mode deformation in axial direction when an excitation voltage generated by signal generator 16 is applied to the piezoelectric transducer 15.

In another preferred embodiment piezoelectric transducer 15 and its mechanical coupling to pipetting needle 12 are adapted for causing a bending mode vibration of the pipetting needle. This is achieved by applying to the piezoelectric transducer a driving signal which causes a bending mode vibration of needle 12.

In a preferred embodiment electromechanical transducer 15 is a single piezoelectric transducer which is simultaneously used as actor, i.e. for causing a vibration of said pipetting needle in response to a driving signal provided by signal generator 16, and also as sensor, i.e. for providing a measured signal which is representative of and corresponds to the vibration of the said needle. In this case the level sensor apparatus preferably comprises a conventional measuring circuit for measuring electrical current flowing through said single piezoelectric transducer 15 and for providing the measured electrical current as vibration signal 35, i.e. as a signal representative of the mechanical vibration of the pipetting needle. Advantages of this embodiment of transducer 15 include its simple structure (it comprises just one piezoelectric transducer and only two connection leads) and relatively low price.

Figure 2:
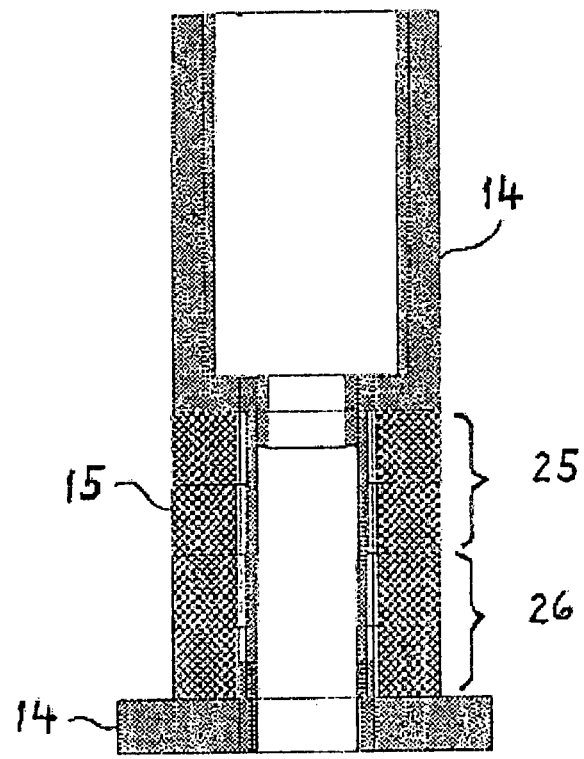
FIG. 2 is a cross-sectional view of the electromechanical transducer and the needle holder shown in FIG. 1.

In another preferred embodiment electromechanical transducer 15 has the structure shown in FIG. 2 which shows the transducer 15 and needle holder 14. In this case electromechanical transducer 15 comprises a first piezoelectric transducer 25 used as actor and a second piezoelectric transducer 26 used as sensor. Piezoelectric transducer 25 is electrically connected with and receives a driving signal from signal generator 16. Piezoelectric transducer 26 provides an electrical output signal which is representative of the mechanical vibration of pipetting needle 12. This signal is transmitted to electronic circuit 17. The advantage of this embodiment of transducer 15 is that it provides vibration signals of better quality, i.e. signals having a higher signal-to-noise ratio and makes it thereby possible to achieve level detection with higher accuracy and reliability.

In the embodiment shown in FIG. 2, needle holder 14 is formed of an upper part and a lower part. These parts are connected with each other by a bolted connection which allows exertion of a predetermined preloading on electromechanical transducer 15 which is inserted between those parts of needle holder 14. The upper end of needle 12 is bolted on the upper part of needle holder 14.

Transport system 21 comprises an arm 24 which carries needle holder 14 and serves for moving pipetting needle 12 with respect to vessel 11.

Figure 3:
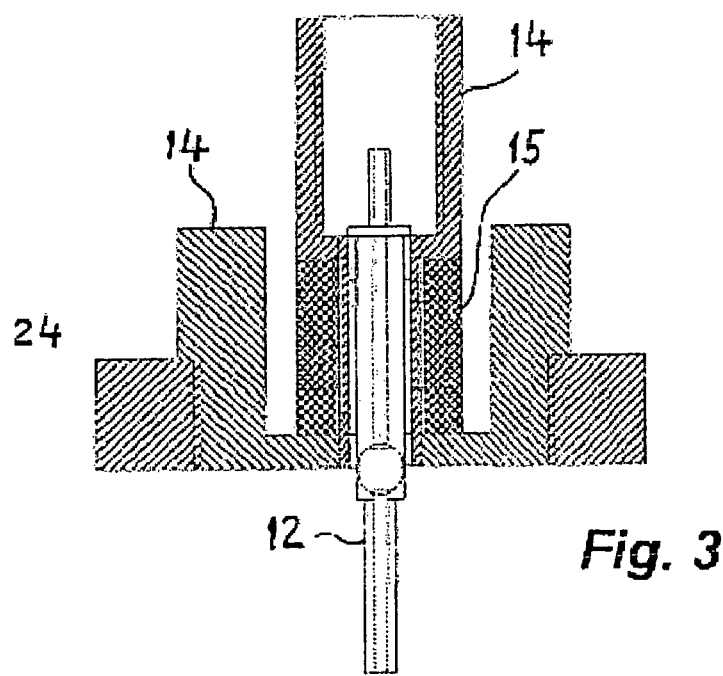
FIG. 3 is an enlarged view of a part of the block diagram shown by FIG. 1.

FIG. 3 shows a cross-sectional view of arm 24, needle holder 14, electromechanical transducer 15 and of a portion of needle 12.

Signal generator 16 generates a driving signal and applies this signal to electromechanical transducer 15 or to the actor part thereof for causing vibration of pipetting needle 12 at one of the resonance frequencies of the sensor head.

In a preferred embodiment signal generator 16 comprises a control circuit for bringing the frequency of the driving signal provided by signal generator 16 back to the resonance frequency of the vibration mode of pipetting needle 12 if and when there is a change in the boundary conditions, e.g. a change of the environment temperature or a change of the mechanical coupling between electromechanical transducer 15 and pipetting needle 12. The latter control circuit preferably operates according to a predetermined algorithm, e.g. software which ensures that the frequency of vibration is a chosen resonance frequency and is brought back to that frequency value if the frequency of vibration is modified by a change in the boundary conditions. The adjustment of the frequency of the driving signal by means of the control circuit just mentioned is performed immediately before each level detection process carried out with the level sensor apparatus according to the invention.

Electronic circuit 17 for level detection receives a vibration signal output from sensor part 26. Electronic circuit 17 comprises means for evaluating the variation of a parameter of the latter vibration signal with time, e.g. for evaluating the variation of the phase or the variation of the amplitude of the vibration signal with time, for detecting contact of the pipetting needle with the surface 27 of liquid 28 contained in vessel 11 and for providing a resulting signal representative of the result of said evaluation.

In a preferred embodiment the apparatus shown in FIG. 1 further comprises means (not shown) for measuring electrical current flowing through a piezoelectric transducer 15 when the latter is used as sensor and when the same piezoelectric transducer 15 is used as sensor, but also as actor.

Figure 4:
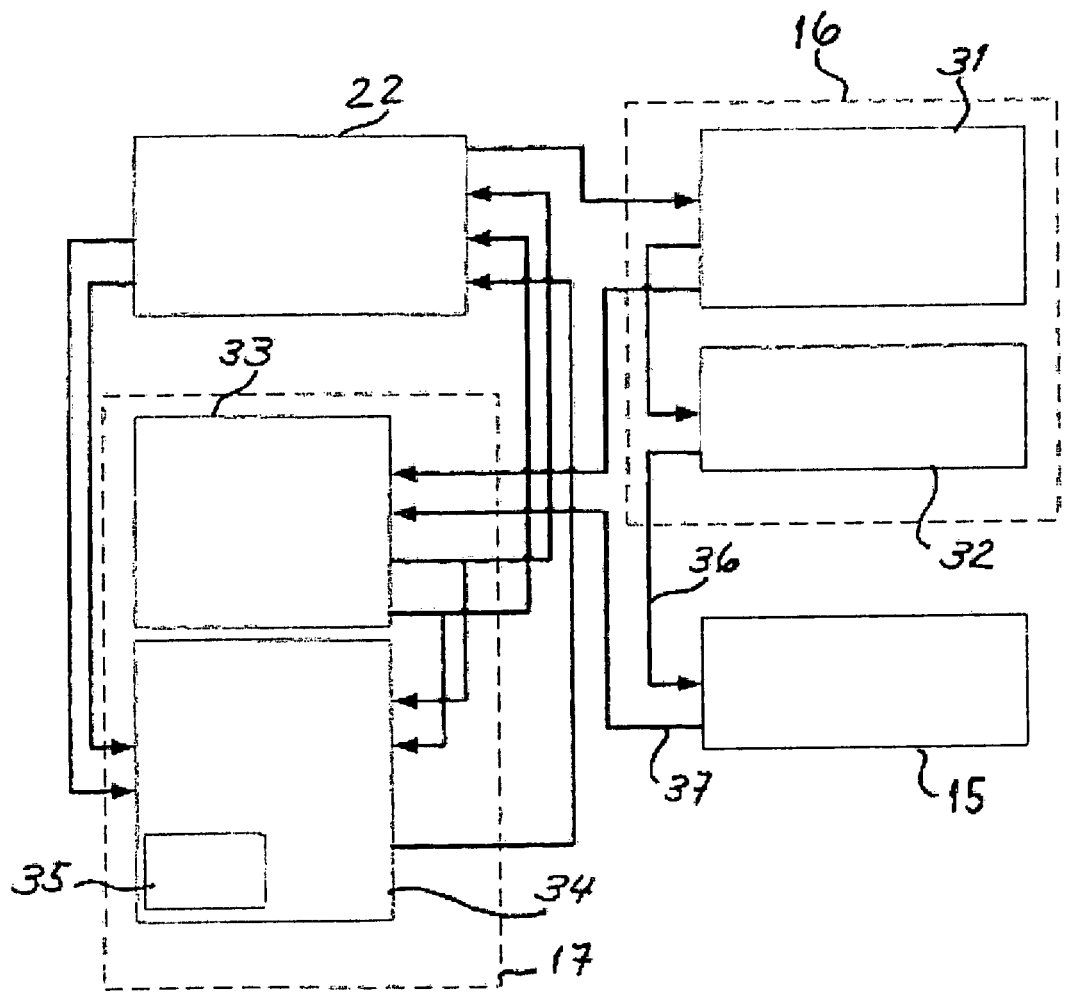
FIG. 4 is a block diagram showing the control unit, the signal generator, the electronic circuit and the electromechanical transducer shown in FIG. 1.

In a preferred embodiment the apparatus shown in FIG. 1 further comprises means (not shown) for measuring a voltage across sensor part 26 of piezoelectric transducer 15. FIG. 4 shows a block diagram showing more in detail the structure of control unit 22, signal generator 16, electronic circuit 17 and electromechanical transducer 15.

As shown in FIG. 4, signal generator 16 comprises a driving signal generator 31 and a high voltage amplifier 32, and electronic circuit 17 comprises a lock-in amplifier 33 and a signal processor 34. The drive signal provided by signal generator 16 is fed via lead 36 to an input of actor part 25 of electromechanical transducer 15. The vibration signal provided by sensor part 26 of electromechanical transducer 15 is fed via lead 37 to an input of lock-in amplifier 33. Other leads shown in FIG. 4 provide the necessary electrical connections between blocks 22, 33, 31 and 32.

Lock-in amplifier 33 receives as input signals a reference signal provided by signal generator 31 and an electrical output signal provided by electromechanical transducer 15. The reference signal applied to an input of lock-in amplifier 33 has a frequency $f_R$ which is a predetermined resonance frequency of the sensor head comprising pipetting needle 12, holder 14 of the pipetting needle and electromechanical transducer 15. The output signal provided by electromechanical transducer 15 is representative of the vibrations of pipetting needle 12 and is therefore called vibration signal. This vibration signal is e.g. a signal representative of electrical current flowing through piezoelectric transducer 15 when a single piezoelectric transducer is used as sensor and actor, or a voltage measured across a piezoelectric transducer 26 (shown in FIG. 2) used as sensor. Lock-in amplifier 33 measures the latter vibration signal and provides two output signals that are applied as corresponding input signals to signal processor 34. One of these input signals is a signal representative of the phase of the vibration signal, the other input signal is a signal representative of the amplitude of the vibration signal.

Within the scope of the instant invention vibration of pipetting needle 12 at one length mode resonant frequency is achieved by the above mentioned means. The frequency and the quality (i.e. damping) of the resonance of needle 12 are dependent on the material and geometry of the needle and on the boundary conditions. If the tip end 23 of needle 12 touches a liquid surface, the boundary condition changes and the resonant frequency and the quality of the resonance change as well.

Figure 5:
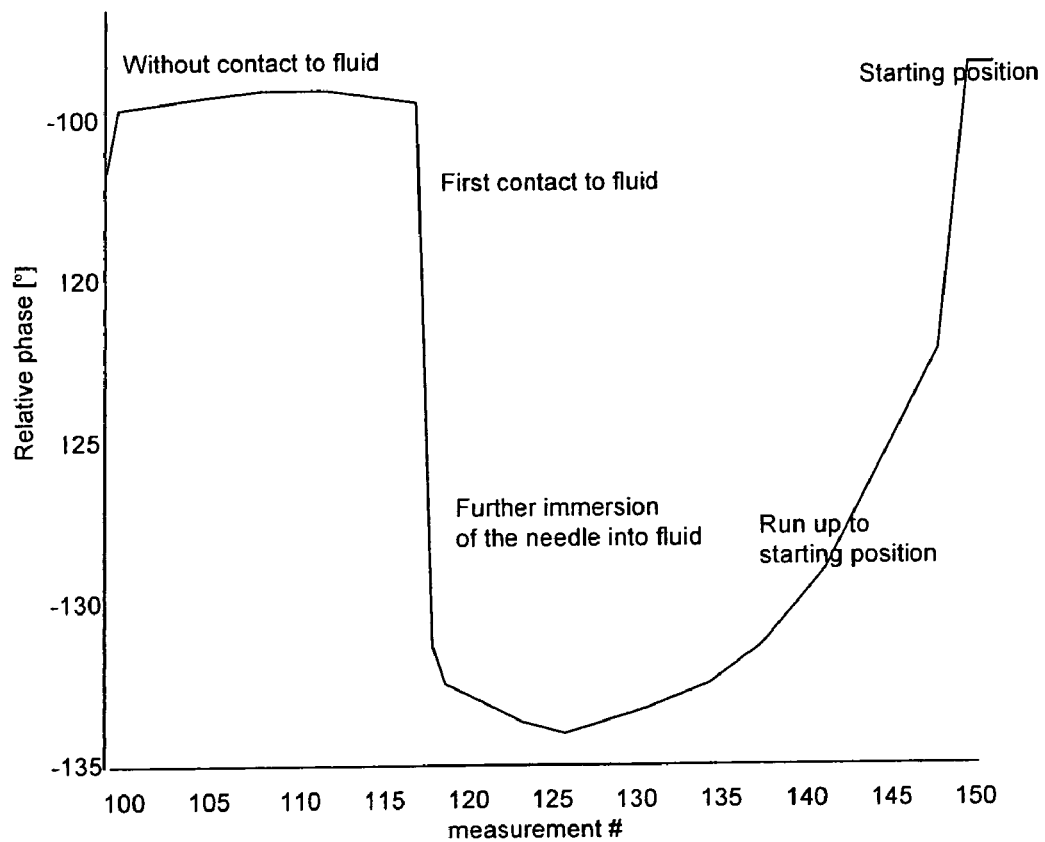
FIG. 5 is a graph showing exemplary jumps in the variation of the phase of a vibration signal with time as a pipetting needle is subject to length mode vibration.

If the vibration of needle 12 is caused by a driving signal having a fixed frequency, a change of the boundary conditions, e.g. a contact of needle 12 with a liquid in vessel 11, produces jumps in amplitude and phase of the vibration signal. FIG. 5 shows for instance typical jumps in the variation of the phase (indicated in degrees) of the vibration signal with time as a pipetting needle subject to length mode vibration with a resonance frequency of 69.14 kHz is moved towards, into and out of a liquid in vessel.

According to the invention such jumps are criteria for the detection of the liquid surface. The jumps in the variation of amplitude and/or phase of the vibration signal with time are detected by electronic circuit 17 which for this purpose preferably comprises means for forming signals which correspond to the first derivative with respect to time of the variation of the amplitude of the vibration signal and/or means for forming signals which correspond to the first derivative with respect to time of the variation of the phase of the vibration signal, and means for detecting the point of time a signal representative of one of those first derivatives with respect to time exceeds or falls below a predetermined threshold value.

Figure 6:
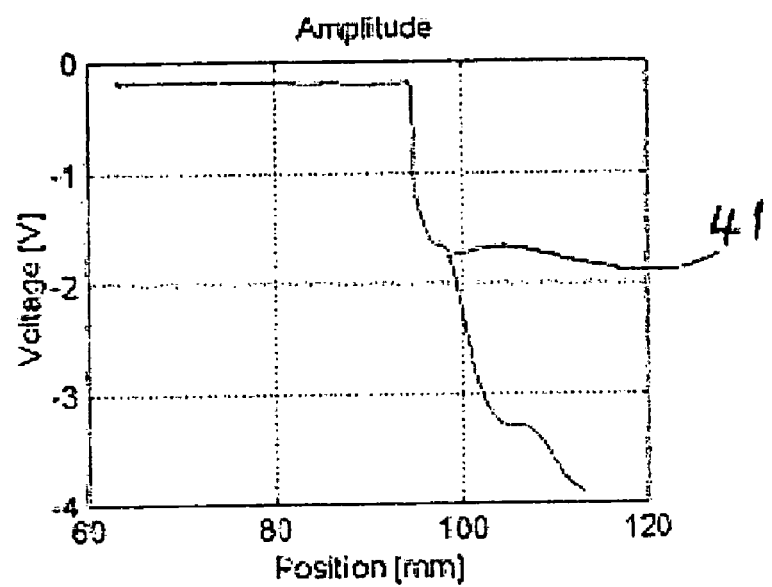
FIG. 6 is a graph showing an example of a variation of an electrical signal representative of the amplitude of a vibration signal in function of the position of the tip of a pipetting needle.

FIG. 6 shows an example of the variation of an electrical signal 41 representative of the amplitude of the vibration signal as a function of the position of the tip of pipetting needle 12 as this needle is moved downwards with a constant velocity and starting at point above the liquid surface in vessel 11. Under these conditions FIG. 6 shows an example of the variation with time of an electrical signal 41 representative of the amplitude of the vibration signal.

Figure 7:
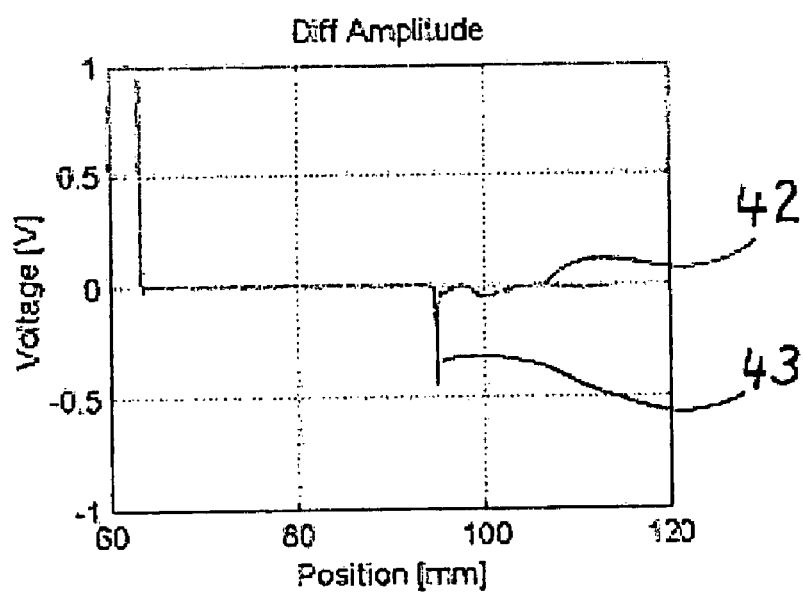
FIG. 7 is a graph showing an example of a variation of an electrical signal representative of a first derivative of the electrical signal represented in FIG. 6 as a function of the position of the tip of the pipetting needle.

FIG. 7 shows the variation of an electrical signal 42 representative of the first derivative of electrical signal 41 as a function of the position of the tip of pipetting needle 12 as this needle is moved downwards with a constant velocity and starting at a point above the liquid surface in vessel 11. Under these conditions FIG. 7 shows an example of the variation with time of an electrical signal 42 representative of the first derivative of electrical signal 41.

From FIGS. 6 and 7 it is apparent that detection of the point of time at which a jump of the amplitude of the vibration signal occurs can be detected with higher accuracy by detecting a corresponding peak 43 of electrical signal 42 which is representative of the variation with time of the first derivative of the amplitude of the vibration signal.

Figure 8:
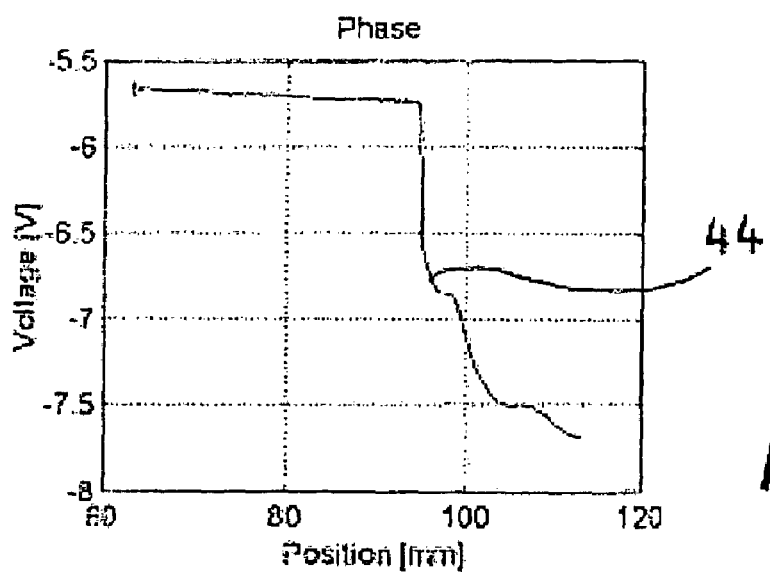
FIG. 8 is a graph showing an example of a variation of an electrical signal representative of the phase of a vibration signal as a function of the position of the tip of pipetting needle.

FIG. 8 shows an example of the variation with time of an electrical signal 44 representative of the phase of the vibration signal as a function of the position of the tip of pipetting needle 12 as this needle is moved downwards with a constant velocity and starting at point above the liquid surface in vessel 11. Under these conditions FIG. 8 shows an example of the variation with time of an electrical signal 44 representative of the phase of the vibration signal.

Figure 9:
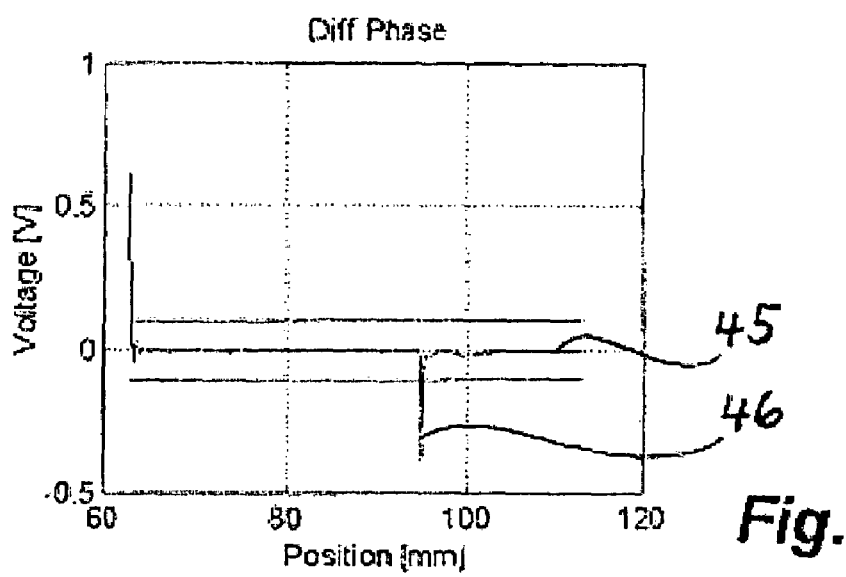
FIG. 9 is a graph showing a variation of an electrical signal representative of a first derivative of electrical signal represented in FIG. 8 as a function of the position of the tip of pipetting needle.
Figure 12:
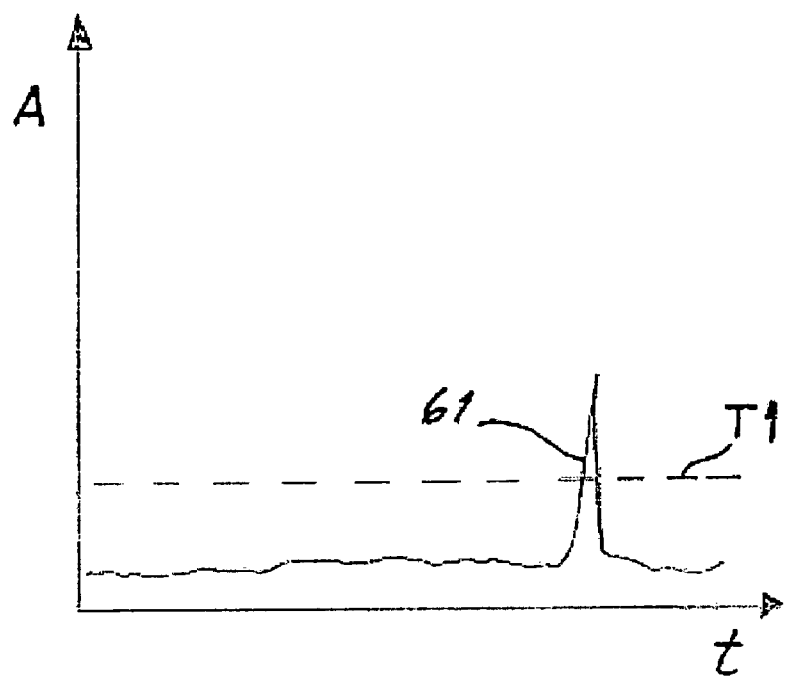
FIG. 12 is a graph showing a vibration signal and a fixed threshold value.
Figure 13:
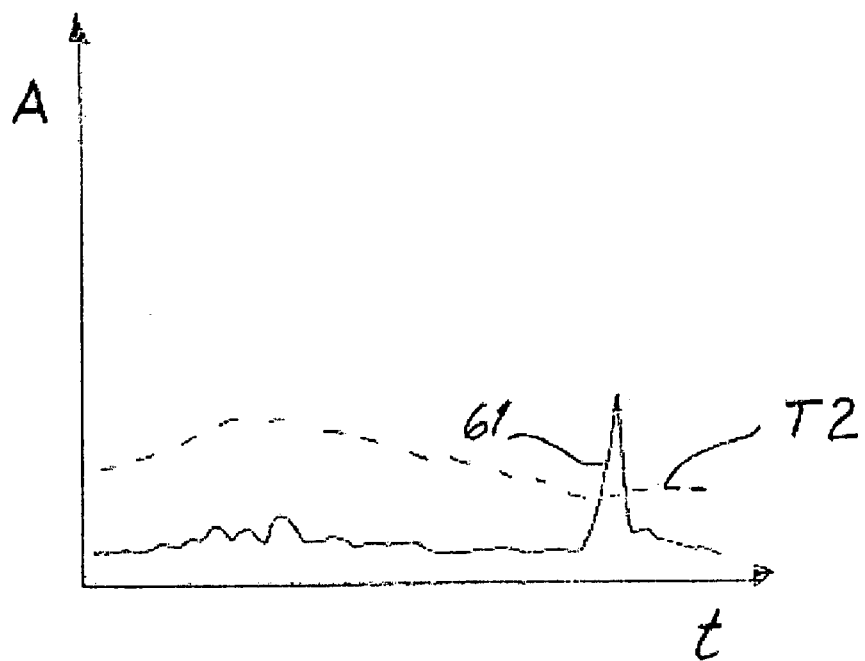
FIG. 13 is a graph showing a vibration signal and a time variable threshold value.

FIG. 9 shows the variation with time of an electrical signal 45 representative of the first derivative of electrical signal 44 as a function of the position of the tip of pipetting needle 12 as this needle is moved downwards with a constant velocity and starting at a point above the liquid surface in vessel 11. Under these conditions FIG. 9 shows an example of the variation with time of an electrical signal 45 representative of the first derivative of electrical signal 44.

From FIGS. 8 and 9 it is apparent that detection of the point of time at which a jump of the phase of the vibration signal occurs can be detected with higher accuracy by detecting a corresponding peak 46 of the variation with time of the first derivative of the phase of the vibration signal.

According to the invention, the point of time at which pipetting needle 12 contacts surface 27 of liquid 28 in vessel 11 is thus accurately detected by electronic circuit 17 which for this purpose detects a jump of the phase or the amplitude of the vibration signal e.g. by detection of one of the above mentioned peaks 43 or 46.

By performing a process similar to the above described method for detecting contact of pipetting needle 12 with liquid 28, the apparatus according to the invention is also able to detect an undesirable contact of pipetting needle 12 with a body, e.g. contact of needle 12 with the bottom wall of vessel 11 which might happen when transport device 21 moves needle 12 downwards in vessel 11. In a preferred embodiment, upon detection of such a contact, electronic circuit 17 provides a corresponding output signal to control unit 22 which in turn causes transport device 21 to stop downward motion of pipetting needle 12.

In a preferred embodiment the frequency of the driving signal provided by signal generator is adjusted to the value of a selected one of the resonance frequencies of the sensor head. This selection is carried out taking into account the variation of the amplitude and phase of the vibration signal with frequency which are e.g. as shown by FIGS. 10 and 11.

FIG. 10 shows an amplitude vs. frequency diagram 51 for the vibration signal of a sensor head including a pipetting needle and an amplitude vs. frequency diagram 52 for the vibration signal of a sensor head without a pipetting needle.

FIG. 11 shows a phase vs. frequency diagram 54 for the vibration signal of a sensor head including a pipetting needle and a phase vs. frequency diagram 55 for the vibration signal of a sensor head without a pipetting needle.

As can be appreciated from FIGS. 10 and 11 for a sensor head taken as example, the amplitude vs. frequency diagram 51 of the vibration signal reaches a maximum 53 at a frequency that lies approximately 200 Hz higher than a maximum 56 of the phase vs. frequency diagram 54 of the vibration signal.

From FIGS. 10 and 11 it can be also appreciated that when the frequency of the driving signal provided by signal generator 16 to electromechanical transducer 15 lies at a first frequency value where the amplitude vs. frequency diagram 51 of the vibration signal reaches a maximum 53, the phase vs. frequency diagram 54 has a larger slope than the amplitude vs. frequency diagram 51. At that resonance frequency it is therefore suitable to detect changes in the phase of the vibration signal in order to detect contact of the tip of pipetting needle with a liquid contained in vessel 11.

From FIGS. 10 and 11 it can be also appreciated that when the frequency of the driving signal provided by signal generator 16 to electromechanical transducer 15 lies at a second frequency value where the phase vs. frequency diagram 54 of the vibration signal reaches a maximum, the amplitude vs. frequency diagram 51 has a larger slope than the phase vs. frequency diagram 54. At that resonance frequency it is therefore possible to detect changes in the amplitude of the vibration signal in order to detect contact of the tip of pipetting needle 12 with a liquid contained in vessel 11.

From FIGS. 10 and 11 it can be also appreciated that when the frequency of the driving signal provided by signal generator 16 to electromechanical transducer 15 lies at a frequency value between the first and second frequency values just mentioned, detection of changes of both the phase or the amplitude of the vibration signal can be used in order to detect contact of the tip of pipetting needle with a liquid contained in vessel 11.

Different vibration modes of the pipetting needle are suitable depending on the kind of obstacles the pipetting needle encounters as it is moved towards a liquid contained in a vessel. The following cases are considered:

1) If the vessel contains no foam, but the pipetting needle has to pierce a closure of the vessel in order to reach the liquid, length mode or bending mode vibration of the needle are both suitable for detecting the liquid surface and for this purpose a corresponding change of the phase of the vibration signal is detected. Since the position of the closure is known to the system, a jump of the phase vibration signal corresponding to contact of the needle with the closure is recognized as such and does not cause generation of an erroneous signal indicating contact of the needle with the liquid.

2) If the vessel is open (i.e. without a closure of its top opening), but the pipetting needle has to pass through foam in order to reach the liquid, use of length mode vibration of the needle is preferable for detecting the point of time at which the needle contacts the surface of the liquid and for this purpose a corresponding change of the phase of the vibration signal is detected. However, if instead of liquid detection it is desired to detect contact of the needle with foam, then it is preferable to apply a bending mode vibration of the needle and to detect a corresponding change of phase of the vibration signal.

3) If the pipetting needle has to pierce a closure of the vessel in order to reach the liquid, and if the vessel contains foam in the space between the closure and the free surface of the liquid, length mode vibration of the needle is suitable for detecting the point of time at which the needle contacts the free surface of the liquid and for this purpose a corresponding change of the phase of the vibration signal is detected. However, if instead of liquid detection it is desired to detect contact of the needle with foam, then it is preferable to apply a bending mode vibration of the needle and to detect a corresponding change of the phase of the vibration signal.

4) If the vessel is open (i.e. without a closure of its top opening) and contains no foam, length mode or bending mode vibration of the needle are both suitable for detecting the point of time at which the needle contacts the free surface of the liquid and for this purpose a corresponding change of the phase of the vibration signal is detected.

In each of the above described cases 1) to 4) instead of detecting a change of the phase of the vibration signal, a corresponding change of the amplitude of the vibration signal can be detected in order to determine the point of time at which the needle contacts the liquid.

While piercing cap 13 with needle 12, the phase of the vibration signal changes strongly due to the cap's influence. However, when needle 12 has pierced cap 13 and a certain distance is reached between the cap and the tip 23 of needle 12, the phase of the vibration signal becomes again fairly constant and the liquid surface can be detected again by detecting a jump in the phase of the vibration signal when needle 12 contacts the surface of liquid 28 in vessel 11. Therefore needle 12 has to move some distance through cap 13 before a reliable liquid level detection is possible again.

In a preferred embodiment the electronic circuit 17 for level detection comprises means for evaluating the variation of said vibration signal with time and these means are associated with a computer program or software for detecting the level of the surface 27 of liquid 28 contained in vessel 11 in FIG. 1. The latter software means preferably include means for detecting the point of time at which a parameter of the vibration signal 61 reaches a threshold value. In one embodiment this threshold value has a predetermined fixed value T1 shown schematically in FIG. 12. In another embodiment the threshold value has a value T2 variable with time shown schematically in FIG. 13. Threshold value T2 is calculated and generated taking into account various factors like history of measurement results previously obtained, specific situation and specific needle type.

In a preferred embodiment electronic signal processor 34 of circuit 17 comprises a data storage 35 for receiving and storing available information on the shape, dimensions and vertical position of a removable cap or cover closure 13 which closes an opening at the top of vessel 11. When processing a vibration signal, signal processor 34 preferably takes the latter information into account in the process of level detection according to the invention. Use of this additional information improves the capability and reliability of the level detection means for selectively detecting the level of the liquid surface in vessel 11.

In a preferred embodiment, information on the amount of liquid contained in vessel 11 is provided by control unit 22 and stored in data storage 35. An estimated value of the vertical position of the liquid surface in vessel 11 is calculated e.g. in electronic circuit 17 from information stored in data storage 35 on the amount of liquid contained in vessel 11 in combination with information available on the shape, dimensions and vertical position of vessel 11. Use of the above mentioned estimated value of the vertical position of the liquid surface in vessel 11 in signal processor 34 further improves the capability and reliability of the level detection means for selectively detecting the level of the liquid surface in vessel 11. On the basis of additional information just mentioned a time window is defined within which the electronic circuit for level detection is activated. Monitoring of the level detection signal within this time window indicates the point of time at which the tip of needle 12 contacts the liquid in vessel 11. From this indication the actual vertical position of needle 12 is determined. The level of liquid in vessel 11 is then calculated taking into account the actual vertical position of needle 12.

Figure 14:
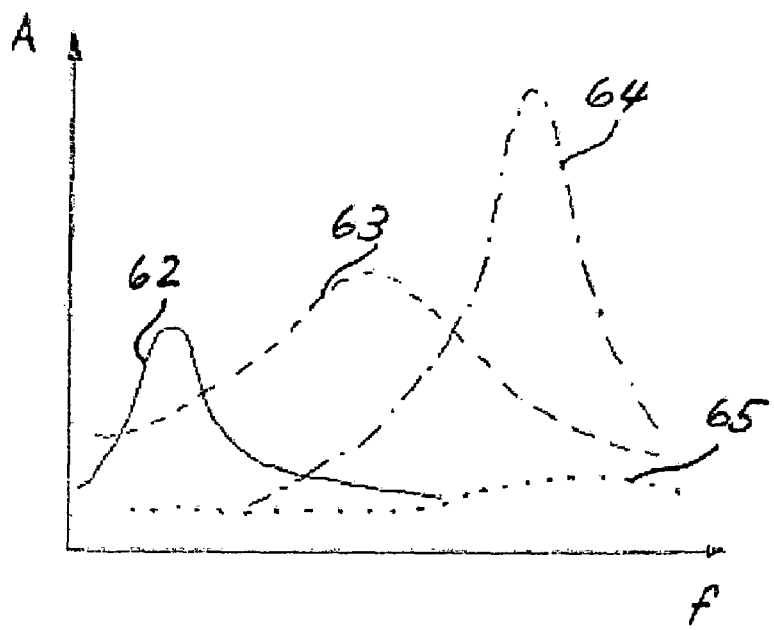
FIG. 14 is a graph showing various resonance curves for different sensor heads.

In a preferred embodiment the apparatus shown in FIG. 1 further comprises means for adapting the apparatus for operating with different types of pipetting needles, i.e., with pipetting needles having different resonance frequencies or modes. FIG. 14 shows schematically different resonance curves 62, 63, 64 of different pipetting needles 12.

In FIG. 14, 62 is a resonance curve for a sensor head including a first type of a pipetting needle, 63 is resonance curve for a sensor head including a second type of a pipetting needle, 64 is a resonance curve for a sensor head including a third type of a pipetting needle and 65 is a resonance curve for a sensor head without a pipetting needle.

The above mentioned adaptation of the apparatus shown by FIG. 1 for operating with different types of pipetting needles is achieved by automatically finding for a given embodiment of a pipetting needle 12 a vibration mode thereof (length or bending mode vibration) and a resonant frequency for that vibration mode which are suitable for detecting the level of liquid in the vessel. For this purpose control circuit 22, driving signal generator 16 and electronic circuit 17 are adapted for performing a frequency sweep of the driving signal, which is applied to the electromechanical transducer for causing vibration of a particular type of pipetting needle installed in the pipetting apparatus, measuring resonance frequency 35 values of that pipetting needle and comparing the results with resonance frequency values previously measured and stored for each one of different needle types. Those values are stored in a look-up table, e.g., in data storage 35. These tables show a resonance modus for each resonance frequency. By means of these tables, the system automatically recognizes which needle type is being used and applies to the piezoelectric transducer a drive signal having a suitable frequency for causing vibration of the pipetting needle with a predetermined resonance mode. On the basis of previous knowledge about the order in which the resonance points arise in the various modes for a given type of pipetting needle, the above mentioned frequency sweep makes it possible to find a suitable vibration mode and resonance frequency for a given embodiment of pipetting needle. This makes it possible to adapt the frequency of the driving signal to a given embodiment of pipetting needle used.

FIG. 14 also shows a resonance curve 65 for a sensor head which does not include a pipetting needle. As can be appreciated from FIG. 14, curve 65 considerably differs from resonance curves 62, 63, 64 for sensor heads including a pipetting needle. By performing a frequency sweep of the above mentioned kind, the apparatus according to the invention is able to measure a resonance curve and by comparison of the measured values with values stored in data storage 35 for previously measured curves 62, 63, 64, the apparatus is able to ascertain whether the sensor head being used includes a pipetting needle 12 or whether such a needle is missing; in other words, whether a pipetting needle 12 is present or absent in the structure of the sensor head.

Figure 15:
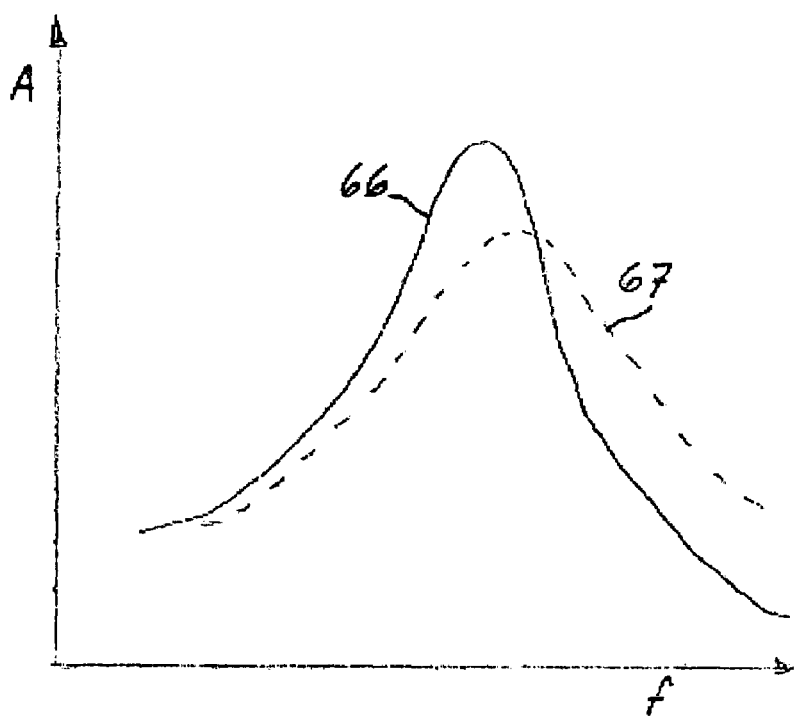
FIG. 15 is a graph showing resonance curves for a sensor head with a properly mounted pipetting needle and for a sensor head with a deformed or defective pipetting needle.

FIG. 15 shows a resonance curve 66 measured with a sensor head including a properly mounted pipetting needle which does not have any deformation or defect and a resonance curve 67 measured with a sensor head including a pipetting needle which has some deformation or defect or is improperly mounted. By performing a frequency sweep of the above mentioned kind, the apparatus according to the invention is able to measure a resonance curve 67 and by comparison of measured values with values stored in data storage 35 for a previously measured curve 66, the apparatus is able to ascertain whether the sensor head being used includes a pipetting needle 12 which is in order or whether that needle has some deformation or defect or is improperly mounted. Moreover the latter comparison also allows a determination of whether such a deformation or defect exceeds a predetermined amount.

Figure 16:
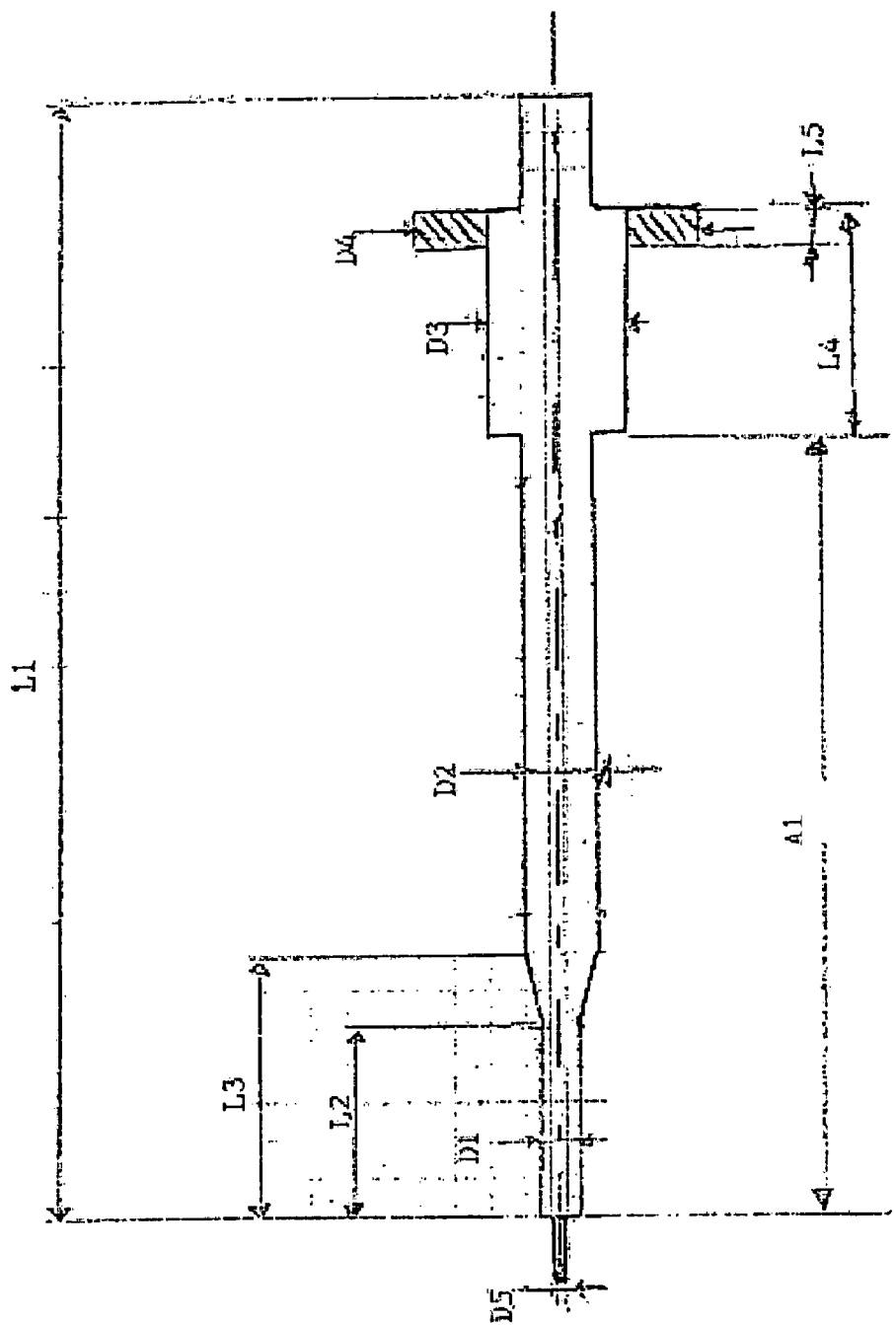
FIG. 16 is a schematic showing shape and dimensions of a first embodiment of a pipetting needle.

A first example of a pipetting needle 12 used in the above described apparatus is schematically represented in FIG. 16. The dimensions of this pipetting needle are as follows:

| Dimension | Size in millimeter |
| --- | --- |
| A1 | 69 |
| L1 | 86 |
| L2 | 5 |
| L3 | 9 |
| D1 | 0.9 |
| D2 | 1.5 |
| D3 | 3 |
| D4 | 5 |
| L4 | 13.5 |
| L5 | 0.5 |
| D5 | 0.6 |

Figure 18:
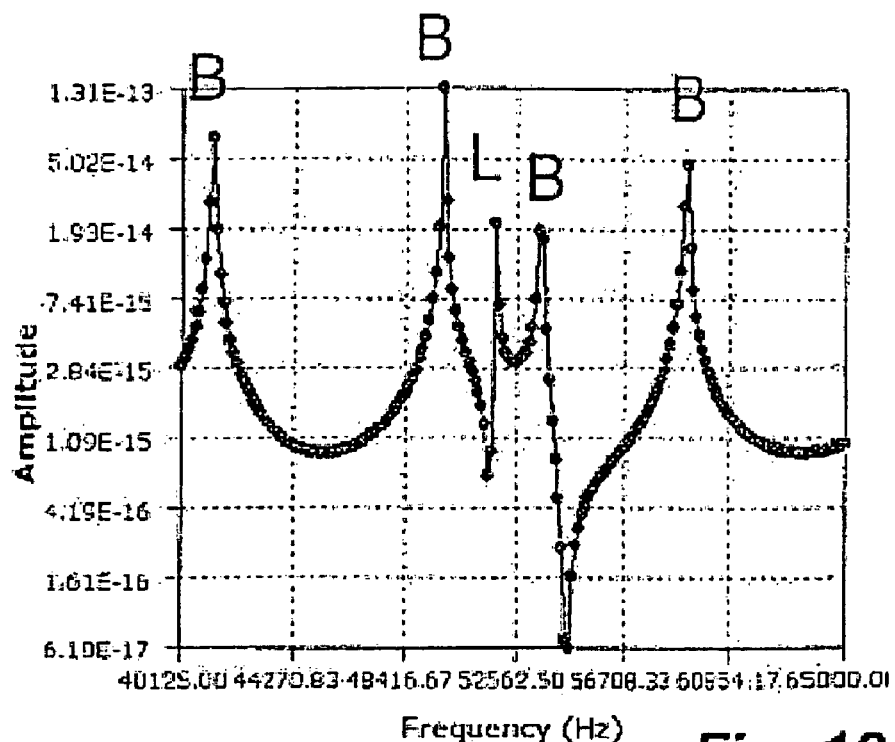
FIGS. 18-21 are graphs showing vibration amplitudes as a function of vibration frequency for pipetting needles having different lengths.
Figure 19:
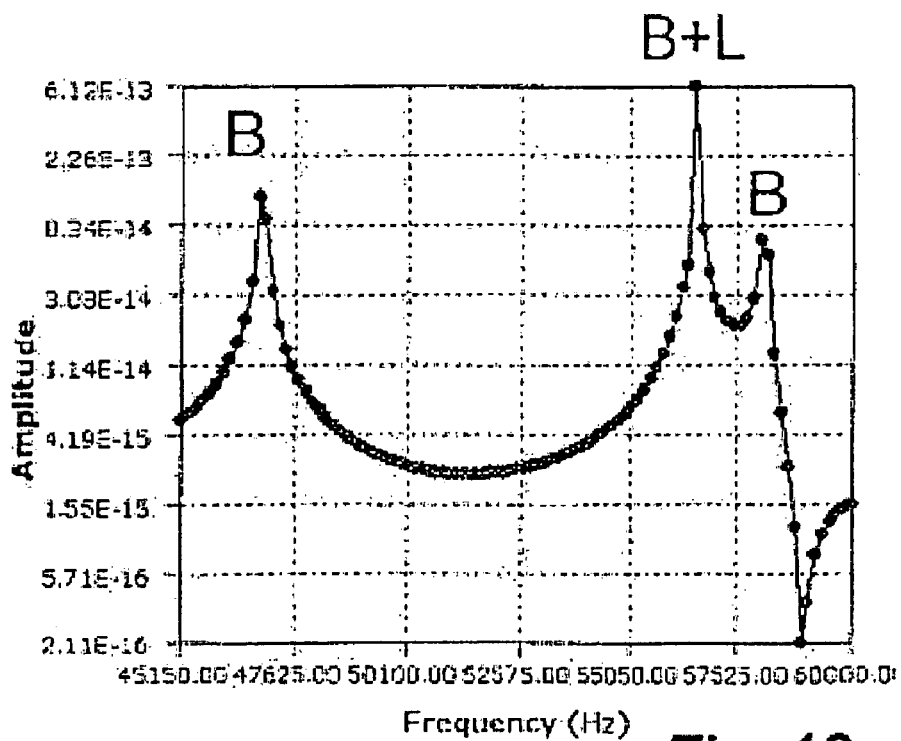
Figure 20:
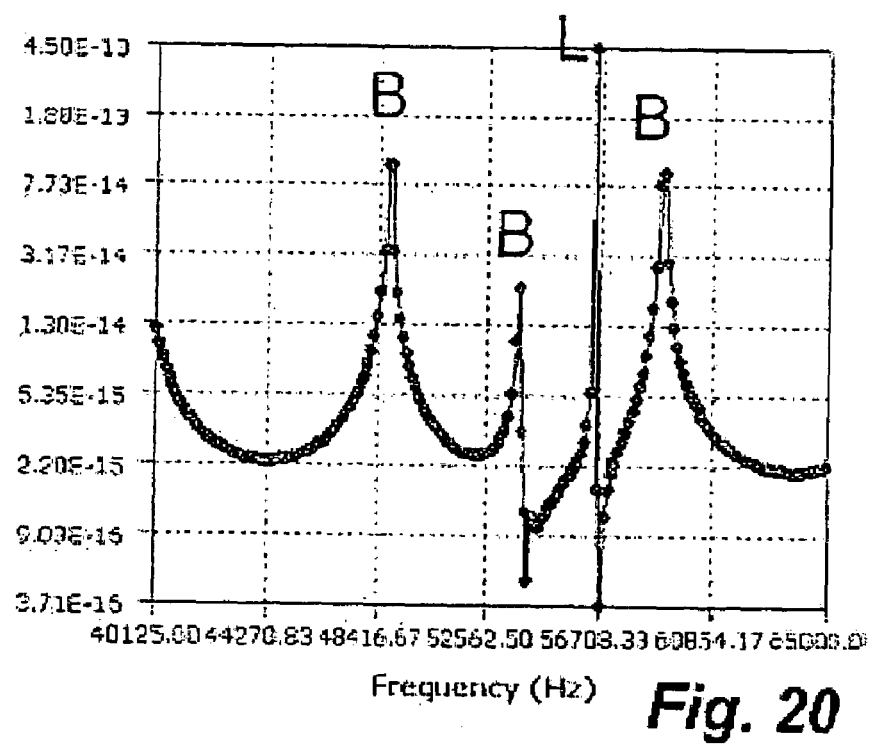
Figure 21:
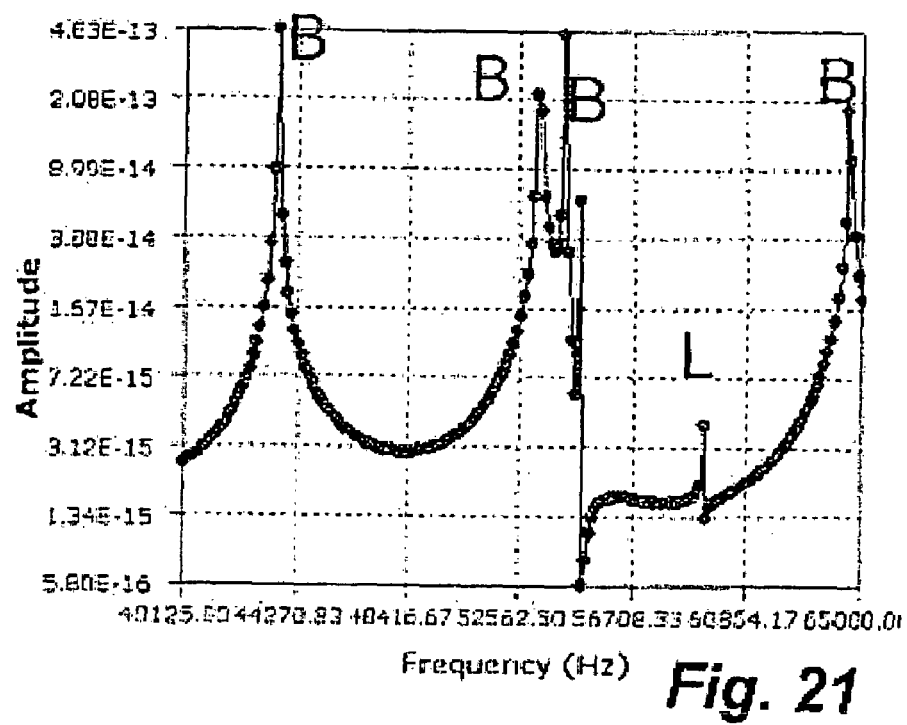

Pipetting needles 12 having different dimensions have different vibration spectra. FIGS. 18 to 21 show spectra of pipetting needles having different dimensions A1. In FIGS. 18 to 21, the amplitudes are indicated in arbitrary units. The spectra represented in FIGS. 18 to 21 show resonance points for bending mode B and length mode L vibration. FIG. 18 shows the vibration spectrum of a pipetting needle having the above mentioned dimensions wherein A1=69 millimeter. FIG. 19 shows the vibration spectrum of a pipetting needle having the above mentioned dimensions wherein A1=66 millimeter. FIG. 20 shows the vibration spectrum of a pipetting needle having the above mentioned dimensions wherein A1=63 millimeter. FIG. 21 shows the vibration spectrum of a pipetting needle having the above mentioned dimensions wherein A1=60 millimeter.

For the purpose of level detection according to the invention it is advantageous to use a pipetting needle having a vibration spectrum wherein the resonance points for bending mode B and length mode L vibration are clearly separated from each other. In the embodiment of pipetting needle 12 shown in FIG. 16 the tip 23 of needle has the cylindrical shape shown and that tip is shown to have a diameter D5.

Figure 17:
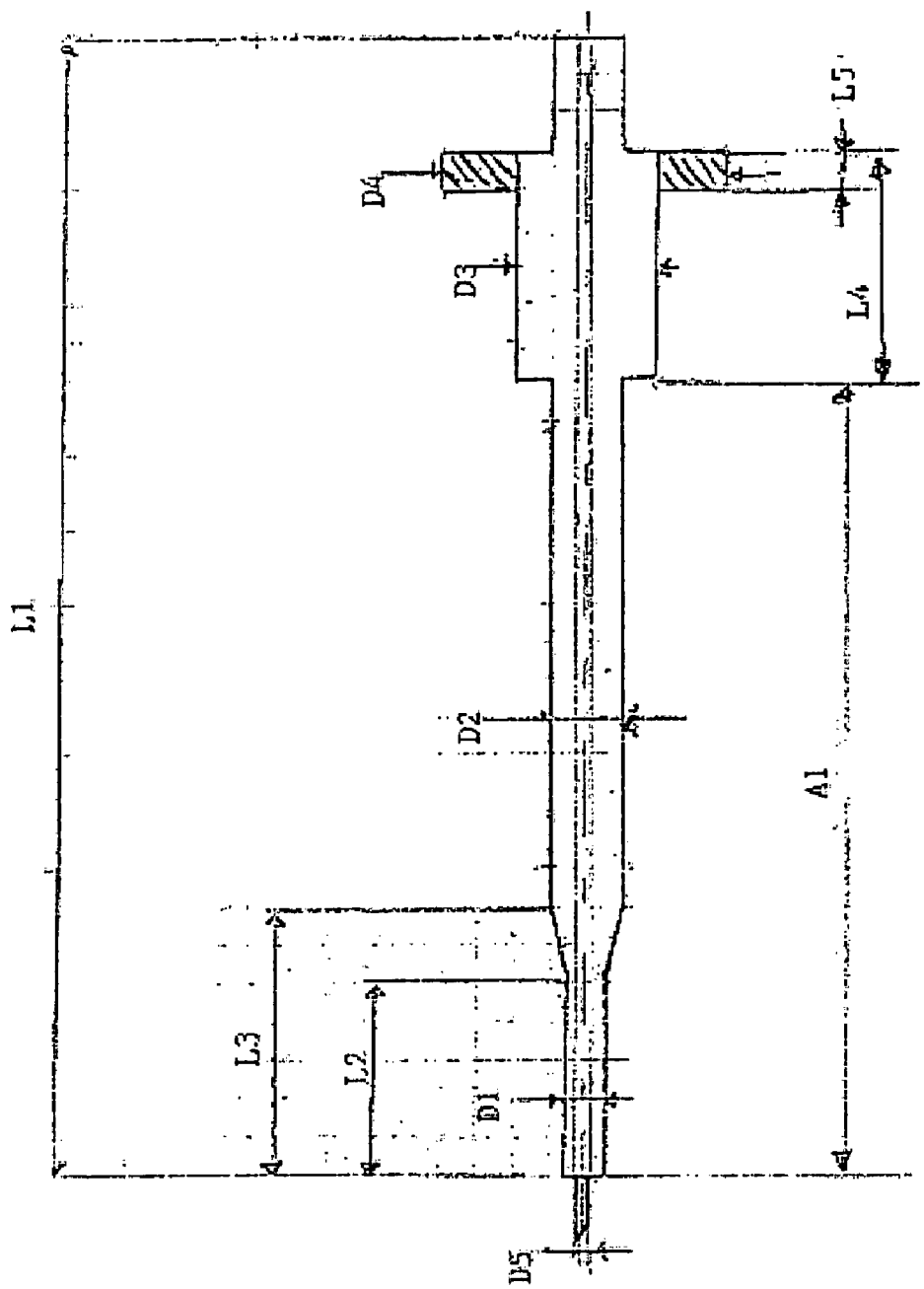
FIG. 17 is a schematic showing shape and dimensions of a second embodiment of a pipetting needle.

Another embodiment of pipetting needle 12 is shown in FIG. 17. This embodiment has a similar shape and dimensions as the embodiment shown in FIG. 16, but the tip of the needle has a sharp end which is suitable for piercing a closure of a vessel.

Although preferred embodiments of the invention have been described using specific terms, such description is for illustrative purposes only, and it is to be understood that changes and variations may be made without departing from the spirit or scope of the following claims.

The invention claimed is:

1. A level sensor apparatus for detecting contact of a pipetting needle with a liquid contained in a vessel, said apparatus comprising:
   a sensor head having a mechanical resonance frequency and including:
      a pipetting needle,
      a needle holder for holding the pipetting needle, and
      an electromechanical transducer mechanically coupled with the pipetting needle;
   an electrical signal generator for generating a driving signal and for applying the signal to the electromechanical transducer to cause vibration of said pipetting needle at the resonance frequency;
   a measurement device for measuring a parameter of a vibration signal provided by the electromechanical transducer, the vibration signal being representative of a vibration of the pipetting needle when it is driven by the driving signal; and
   electronic circuit for (i) evaluating variation of the vibration signal with time, (ii) detecting contact of the pipetting needle with a liquid contained in the vessel, and (iii) providing a resulting signal representative of the result of said evaluation.

2. A level sensor apparatus according to claim 1, wherein said electromechanical transducer is a piezoelectric transducer.

3. A level sensor apparatus according to claim 2, wherein the measurement device measures electrical current through the piezoelectric transducer.

4. A level sensor apparatus according to claim 1, wherein the electromechanical transducer comprises a first piezoelectric transducer used as an actor and a second piezoelectric transducer used as a sensor.

5. A level sensor apparatus according to claim 1, wherein the electronic circuit comprises means for evaluating the variation of the phase of said vibration signal with time.

6. A level sensor apparatus according to claim 1, wherein the electronic circuit comprises means for evaluating the variation of the amplitude of said vibration signal with time.

7. A level sensor apparatus according to claim 1, wherein the electronic circuit comprises means for taking into account available information on the shape, dimensions and vertical position of an element closing an opening at the top of the vessel.

8. A level sensor apparatus according to claim 1, wherein the electronic circuit comprises means for taking into account available information on a vertical position of a liquid surface in said vessel.

9. A level sensor apparatus according to claim 8, wherein the electronic circuit comprises computer software for calculating the vertical position of the liquid surface in the vessel based on information available regarding an amount of liquid contained in the vessel in combination with information available regarding shape, dimensions and vertical position of the vessel.

10. A level sensor apparatus according to claim 1, wherein the electromechanical transducer and its mechanical coupling to the pipetting needle are adapted for causing a length mode vibration of the pipetting needle.

11. A level sensor apparatus according to claim 1, wherein the electromechanical transducer and its mechanical coupling to the pipetting needle are adapted for causing a bending mode vibration of the pipetting needle.

12. A level sensor apparatus according to claim 1, wherein the sensor head is configured for substantially maximizing the amplitude of the vibration at the free tip of the pipetting needle at the resonance frequency.

13. A level sensor apparatus according to claim 1, further comprising program logic for automatically finding a vibration mode and a resonant frequency for that vibration mode which are suitable for detecting the surface of liquid in the vessel.

14. A level sensor apparatus according to claim 1, wherein said electrical signal generator comprises a control circuit configured to bring the frequency of the driving signal back to the resonance frequency of the vibration mode of the pipetting needle if a change of boundary conditions causes a change of that resonance frequency.

15. A level sensor apparatus according to claim 14, wherein the control circuit operates according to a predetermined algorithm.

16. A level sensor apparatus according to claim 1, wherein the electronic circuit comprises computer software for directing a process of detecting a surface of said liquid contained in said vessel.

17. A level sensor apparatus according to claim 16, wherein the software for detecting the level of said liquid includes program instructions for detecting a point of time at which a parameter of the vibration signal reaches a threshold value.

18. A level sensor apparatus according to claim 17, wherein the threshold value has a predetermined fixed value.

19. A level sensor apparatus according to claim 17, wherein the threshold value has a variable value.

20. A level sensor apparatus according to claim 1, further comprising means for detecting the presence or absence of the pipetting needle.

21. A level sensor apparatus according to claim 1, further comprising means for detecting a deformation or a defect of the pipetting needle.

22. A level sensor apparatus according to claim 1, further comprising means for detecting an undesirable contact of the pipetting needle with a body.

* * * * *